(12) United States Patent
Grant et al.

(10) Patent No.: US 12,364,665 B2
(45) Date of Patent: Jul. 22, 2025

(54) SOLID DOSE FORMULATIONS FOR NEEDLE-FREE DELIVERY

(71) Applicant: AVAXZIPEN LIMITED, Abingdon (GB)

(72) Inventors: David Andrew Grant, Faringdon (GB); Chris MacGregor, Abingdon (GB)

(73) Assignee: AVAXZIPEN LIMITED, Abingdon (GB)

( * ) Notice: Subject to any disclaimer, the term of this patent is extended or adjusted under 35 U.S.C. 154(b) by 740 days.

(21) Appl. No.: 17/622,578

(22) PCT Filed: Jun. 25, 2020

(86) PCT No.: PCT/GB2020/051541
§ 371 (c)(1),
(2) Date: Dec. 23, 2021

(87) PCT Pub. No.: WO2020/260882
PCT Pub. Date: Dec. 30, 2020

(65) Prior Publication Data
US 2022/0249379 A1    Aug. 11, 2022

(30) Foreign Application Priority Data
Jun. 27, 2019   (GB) .................................... 1909280

(51) Int. Cl.
*A61K 9/20*    (2006.01)
*A61K 39/00*   (2006.01)

(52) U.S. Cl.
CPC ............ *A61K 9/205* (2013.01); *A61K 9/2013* (2013.01); *A61K 9/2018* (2013.01); *A61K 9/2027* (2013.01); *A61K 9/2072* (2013.01); *A61K 39/00* (2013.01)

(58) Field of Classification Search
CPC .... A61K 9/205; A61K 9/2013; A61K 9/2018; A61K 9/2027; A61K 9/2072; A61K 39/00; A61K 38/00; A61K 9/0021; Y02A 50/30
See application file for complete search history.

(56) References Cited

FOREIGN PATENT DOCUMENTS

| EP | 1173151 A1 | 1/2002 |
|---|---|---|
| EP | 2129366 A2 | 12/2009 |
| WO | 2017068351 A1 | 4/2017 |

OTHER PUBLICATIONS

International Search Report and Written Opinion for PCT application PCT/GB2020/051541 mail date Dec. 30, 2020 8 pages.
International Preliminary Report On Patentability for PCT application PCT/GB2020/051541 mail date Jan. 6, 2022, 7 pages.

*Primary Examiner* — Robert A Wax
*Assistant Examiner* — Quanglong N Truong
(74) *Attorney, Agent, or Firm* — Maine Cernota & Curran (57) ABSTRACT

The present disclosure relates to solid dose formulations for needle-free delivery comprising 0.01 to 60 (w/w) of one or more therapeutic agent and/or prophylactic agent; and 40.0% to 99.99% (w/w) of dextran. The invention further concerns methods of producing a solid dose formulation tablet and application its particular medical uses, in particular as a vaccine.

20 Claims, 5 Drawing Sheets

SOLID DOSE FORMULATIONS FOR NEEDLE-FREE DELIVERY

RELATED APPLICATIONS

This application is a national phase application filed under 35 USC § 371 of PCT Application No. PCT/GB2020/051541 with an International filing date of Jun. 25, 2020, which claims priority of GB Patent Application 1909280.8 filed Jun. 27, 2019. Each of these applications is herein incorporated by reference in its entirety for all purposes.

FIELD OF THE INVENTION

This invention relates to novel solid dose formulations for needle-free delivery of therapeutic or prophylactic agents, including immunogenic agents and further to methods of making tablets comprising said solid dose formulations.

BACKGROUND OF THE INVENTION

A common route of administration of therapeutic or prophylactic agents is via parenteral delivery of a liquid formulation using needles and syringes. Parenteral delivery is used for therapeutic or prophylactic agents that are usually poorly absorbed by other routes and/or require rapid delivery.

Among the disadvantages with parenteral delivery via a needle is the associated discomfort and pain for the patient and the health risk caused by used sharps.

A large proportion of therapeutic or prophylactic agents are poorly soluble, often resulting in the production of sub-optimal formulations. In addition, they are typically less stable in aqueous form than in a solid dose form.

Solid dose formulations have been developed as an alternative to liquid formulations; however, these are typically produced for and are mostly intended for oral administration.

Where solid dose formulations comprising therapeutics or prophylactic agents have been developed for use in parenteral administration, it has sometimes still been intended that they will be delivered with the aid of a needle. Such solid dose formulations are produced with the aim of achieving a lean manufacturing process and controlled dissolution after administration. Therefore, the mechanical strength specifications of such solid dose formulations are solely directed to ensure consistent manufacture as an in-process control and to maintain the solid dose formulation during transport and handling prior to, and during administration.

The applicant has previously developed needle-free devices for parenteral delivery of therapeutic or prophylactic compounds in a solid dose formulation in order to overcome the various drawbacks associated with both parenteral delivery and liquid formulations as described above. Such devices are disclosed in the present applicant's previous patent publications including EP1427464, EP1545662, EP1855755 and WO2016/124903.

A fundamental requirement of such needle-free technology is the production of a solid dose form, which comprises the therapeutic or prophylactic agent and has sufficient mechanical strength to penetrate the skin and a size and shape suitable for patient comfort, such as disclosed in EP2129366. For example, the applicant previously developed a solid dose composition described in WO2017/068351, comprising inter alia sodium carboxymethylcellulose salt (CMC), which was determined to have sufficient mechanical strength of at least 80 MPa and to be compatible with the needle-free delivery devices referred to herein before, when manufactured using a wet paste extrusion method followed by drying and cutting to the desired geometry.

Other manufacturing methods have been used in the art in an attempt to produce solid dose formulations with sufficient mechanical strength to enable parenteral administration, such as those described in EP1173151 (Novo Nordisk) and WO2011/042542 (Azurebio).

Tablet compaction is a common method of making solid dose formulations suitable for oral administration, that would typically be of a size and shape that is unsuitable for patient comfort during parental administration. There are examples of 1 mm diameter tablets in literature being trialed but such formulations are not typically suitable for needle-free parenteral delivery due to insufficient mechanical strength: "Development of mini-tablets with 1 mm and 2 mm diameter', Tissen et al, International Journal of Pharmaceutics 416 (2011) 164-170.

It therefore remains highly desirable to provide new processes useful in the manufacture of solid dose formulations for needle-free parental delivery.

The present invention is derived from a need to provide novel solid dose formulations and processes relating to the improved manufacture thereof.

SUMMARY OF THE INVENTION

The invention concerns a solid dose formulation having a compressive strength of equal to or greater than 80 MPa for needle-free delivery, the solid dose formulation comprising: 0.01 to 60% (w/w) of a therapeutic and/or prophylactic agent; and at least 40.0% to 99.99% (w/w) of dextran.

Critically, in order to be suitable for needle-free administration, the solid dose must have sufficient mechanical strength, as recited herein, to withstand the stresses placed on it during subcutaneous delivery and thus enable successful injection of an active substance that is provided within. The solid dose formulation may house a composition including inter alia, the at least one agent.

Surprisingly, compositions of the invention with a percentage of dextran defined in the range above, which is far greater than would typically be found in tableting formulations of the art, achieve the required mechanical and structural integrity for needle-free administration, i.e. compressive strength of 80 MPa or greater.

The applicant considers that publications in the art to date provide little to no data on the production of tablets achieving such a high mechanical strength, especially where it is specific to the technical problems addressed in the present application. This is especially true where excipients used in typical tableting/formulations have been generally used in small quantities for their intended purpose.

The applicant has developed novel formulation in which dextran provides the substantial component or substance of that formulation (with the exception of therapeutic and/or prophylactic agent). When dextran is present in the range of 40.0 to 99.99% (w/w) it confers a significant and useful characteristic to the resulting solid dose, especially in regard to delivery mechanism. The relatively high proportion of dextran, as defined in the range above, has been found to give tablet formulation and in particular microtablet formulation the critical strength parameter required for needle-free parenteral delivery. This is especially true in needle free delivery, for which the invention is considered extremely useful.

In embodiments, dextran provides 40% or more of total composition (w/w). For example, the formulation typically comprises dextran in ranges such as 40-99%, 49.5-99% or 50-99%.

In particular dextran may be provided in the majority, such as 51-99% (w/w) dextran, 63-99% (w/w) dextran, preferably 66-99% (w/w) dextran, 74-99% (w/w) dextran or 82-99% (w/w) dextran. In some cases the formulation may comprise dextran in an upper end range point of up to 90%, 95%, 97%, 98%, 99%, 99.90% or 99.99%. This may be in conjunction with any lower end point in the range and is disclosed as such.

The inventors have further concluded that the technical problem may be solved in another novel and inventive manner wherein the solid dose formulation comprising 0.01% (w/w) of at least one therapeutic and/or prophylactic agent is able to retain a compressive strength of at least about 80 MPa suitable for needle-free delivery.

The inventors have successfully shown that provided at least 25.0% (w/w) of dextran is present in combination with at least one different excipient, or a combination of different excipients, the compressive strength of the resulting composition/formulation can be maintained during strength testing. However, this requires careful selection of excipient (s) and combination used during formulation and is not an arbitrary selection. Typically, the combination of dextran and the one different excipient, or dextran and the combination of further excipients will comprise at least 90-99% of the solid dose formulation to solve the same technical problem and result in a composition with sufficient compressive strength in needle-free delivery.

The invention therefore extends a solid dose formulation having a compressive strength of at least about 80 MPa for needle-free delivery comprising: 0.01%-75.0% (w/w) of at least one therapeutic and/or prophylactic agent; at least 25.0% (w/w) of dextran; and at least 50% (w/w) of at least one, or a combination of two or more, different excipients, excluding dextran. In embodiments, the at least one different excipient, or the two or more excipients combined, excluding dextran, is in the range of 50%-74% (w/w). In other words, the different excipient or total combination of different excipients, that do not comprise the dextran component, comprise 50%-74% (w/w) of the composition. In embodiments the excipient or excipients, excluding dextran, comprise around 74%. These are preferably selected from mannitol and/or trehalose and/or CMC.

Optionally, the formulation of any invention described herein may comprise at least 0.5% (w/w) of a lubricant. In some examples the lubricant may be selected from magnesium stearate or polyethylene glycol (PEG) or lysine. The lubricant is typically provided in at least 0.5% to 1% (w/w) but can be up to 5%. The lubricant may improve the ease of manufacture, for example during the tableting or micro tableting process, to help provide a consistent and reliable output when the formulation is ejected from the press (and with a minimal ejection force, for example).

In embodiments, the formulation may comprise one or more excipient, wherein the excipient(s) is selected from a binder, a bulking agent or a combination thereof.

In examples, the one or more excipient is selected from any of methionine, cysteine, histidine, citric acid, sodium chloride, sodium hydroxide, hydrochloric acid, potassium chloride, tween-20, tween-40, tween-60, tween-80, albumin, mannitol, trehalose, sucrose, sodium carboxymethylcellulose salt (CMC), polylactic-co-glycolic acid (PLGA), polyvinylpyrrolidone (PVP), polyvinyl alcohol (PVA) or polylactic acid (PLA). The selection may include a combination of these excipients and other excipients to provide further advantages to the resulting formulation.

In particular, CMC may also be present in the formulation. It is considered that where the lower end point of the range of percentage of dextran is used, circa 40% or more, a de minimus compressive strength (80 MPa) of the formulation may be maintained by including a percentage of CMC in combination with dextran, e.g. 50% CMC.

The formulation may comprise lower levels of CMC e.g. 10% to 50% (w/w); where higher levels of dextran are used e.g. at least 49.5% (w/w) and one or more other excipients, such as mannitol is present. The combination of dextran and CMC is particularly advantageous when dextran is present at 50% (w/w) or more. In some cases the addition of a further excipient such as mannitol in a specific ratio also permits compressive strength to be maintained. In examples where 10%-50% of CMC is used at least.

In some examples the solid dose formulation provides a single-unit dose. The formulation therefore ensures that consistent dosing is achieved each time, removing variability caused by the technique of the administrator.

Furthermore, compositions have been made with different grades of dextran. These were tested (with mean molecular weights (mw) ranging from 1 kDa to 110 kDa) for impact on compressive strength. In particular, the dextran utilised may be selected from grades with a mean molecular weight that is 10 kDa or more, between 10 kDa and 110 kDa or preferably about 70 kDa, since these embodiments retain a compressive strength of at least 80 MPa.

All such grades may therefore be used in the manufacture of a solid dose formulation to be delivered by a needle-free delivery device of the type described herein.

Of particular advantage is that such as solid dose is reliably able to retain the strength required when sized to the desirable dimensions for optimal needle free delivery. In embodiments the solid dosage form is a microtablet and the benefits of a needle free delivery technique can be fully retained without having to increase the size of the dosage form or change its composition beyond the disclosure herein. In embodiments, the solid dose formulation is elongate; preferably the length to width ratio is in a range between 6:1 and 2:1. Such ratios permit a solid formulation which is more easily delivered. In embodiments, a width of the solid dose formulation is 2 mm or less, preferably 0.85 mm and/or wherein the length of the solid dose formulation is from 2 to 6 mm, preferably 4 mm.

In some embodiments the shape of the solid dose comprises a pointed tip with an internal angle of between 22.5° and 90° to further improve ease of delivery. In most embodiments the total mass of the solid dose formulation is 7 mg or less.

In preferred embodiments the agent is a biological preparation for immunization such as an antigen or other immunostimulating biological component.

In embodiments the at least one agent maybe selected from a vector, a protein, a protein subunit, DNA, RNA, a toxoid or a polysaccharide-antigen conjugate and a checkpoint inhibitor.

In preferred embodiments the formulation may therefore comprise a vaccine. The type of vaccine maybe selected from an attenuated (live) vaccine, an inactivated vaccine, a toxoid vaccine, a subunit or purified antigen vaccine, a conjugate vaccine, a neo-antigen vaccine, an RNA vaccine, a DNA vaccine, heterologous "Jennerian" vaccine, a homologous vaccine and a recombinant vector vaccine.

Where the formulation comprises a vaccine, the formulation may further comprise one or more adjuvants, which may help stimulate the immune response and make the vaccine more effective. Adding adjuvants into traditional attenuated vaccine formulation is aimed at enhancing, accelerating and prolonging the specific immune response to the antigenic agent. Purified subunit or synthetic vaccines that use biosynthetic recombinant may include adjuvants to provoke the desired immune response.

Stabilizers may be used to help the vaccine maintain its effectiveness during storage up until administration. Vaccine stability is essential, particularly where the cold chain is unreliable. Instability can cause loss of antigenicity. Some factors affecting stability of the vaccine are temperature and acidity or alkalinity (pH). Bacterial vaccines can become unstable due to hydrolysis and aggregation of protein and carbohydrate molecules. Stabilizing agents may include $MgCl_2$ (for OPV), $MgSO_4$ (for measles vaccine), lactose-sorbitol and sorbitol-gelatine.

In some embodiments the one (or more) excipients is blended or combined with the dextran by freeze drying or spray drying to first form a powder suitable for subsequent processing into a solid dose form, such as a tablet.

In a further aspect the invention relates to a formulation according to any of the above described embodiments for use as a medicament in the treatment or prevention of a condition, disease or disorder.

In some embodiments, the formulation is for use in the treatment of a cancer associated or attributable to the HPV virus cancers including anal cancer, oropharyngeal cancer, cervical, vulvar and vaginal cancer in women and penile cancer in men.

In some examples the formulation includes a vaccine, or is used to create a vaccination to guard against or treat a human or animal disease, illness or infection. In some examples the disease or disorder is selected from, associated or attributable to cancers, yellow fever, rabies, diphtheria, tetanus, haemophilus influenza type B (Hib), pertussis, pneumococcal diseases, meningococcal diseases, human papilloma viruses (HPV), HTV, HSV2/HSV1, influenza (types A, B and C), para influenza, polio, RSV, rhinoviruses, rotaviruses, hepatitis A, acquired immunodeficiency syndrome (AIDS), anthrax, gastroenteritis, enterovirus diseases, measles, mumps, varicella zoster, glandular fever, respiratory diseases, rubella, human T-cell lymphoma type I (HTLV-I), hepatitis B, hepatitis C, hepatitis D, poxvirus diseases, cholera, Japanese encephalitis, zika, chikungunya, bat lyssavirus, Q fever, rift valley fever, hendra virus, tularaemia, nipah virus, lassa fever, typhoid fever, Crimean-Congo haemorrhagic fever, ebola, plague and shigella, or against veterinary diseases, such as foot and mouth disease (including serotypes O, A, C, SAT-1, SAT-2, SAT-3 and Asia-1), coronavirus, bluetongue, feline leukaemia virus, avian influenza, hendra and nipah virus, pestivirus, canine parvovirus and bovine viral diarrhoea virus.

In some embodiments, the vaccine is a multivalent or combination vaccine. For example, the invention may be used to treat infection by two or more different types of disease or virus, such as measles, mumps and rubella (e.g. MMR vaccine).

In some embodiments the vaccine is selected from an attenuated (live) vaccine, an inactivated vaccine, a toxoid vaccine, a subunit or purified antigen vaccine, a conjugate vaccine, a neoantigen vaccine, an RNA vaccine, a DNA vaccine and a recombinant vector vaccine. Examples of suitable vectors include adenovirus, measles virus, vaccinia virus, poxvirus, alphavirus, vesicular stomatitis virus (VSV) and lentivirus vectors.

In preferred embodiments, where the agent is a prophylactic agent, the prevention is immunization against the condition, disease or disorder.

Other diseases of interest may include MERS (respiratory), Lassa, Nipah, rift valley fever, chikungunya, plague, zika, shigella and flu.

The vaccine of the invention may be used to prevent or treat infection by viruses including one or more of human papilloma viruses (HPV), HTV, HSV2/HSV1, influenza virus (types A, B and C), para influenza virus, polio virus, RSV virus, rhinoviruses, rotaviruses, hepatitis A virus, norwalk virus, enteroviruses, astroviruses, measles virus, mumps virus, varicella-zoster virus, cytomegalovirus, epstein-barr virus, adenoviruses, rubella virus, human T-cell lymphoma type I virus (HTLV-I), hepatitis B virus (HBV), hepatitis C virus (HCV), hepatitis D virus, poxvirus and vaccinia virus.

The vaccine may further be used to provide a suitable immune response against numerous veterinary diseases, such as foot and mouth disease (including serotypes O, A, C, SAT-1, SAT-2, SAT-3 and Asia-1), coronavirus, bluetongue, feline leukaemia virus, avian influenza, hendra and nipah virus, pestivirus, canine parvovirus and bovine viral diarrhoea virus.

In some embodiments, the vaccine is a subunit, conjugate or multivalent or combination vaccine.

The invention further concerns a method of treating or preventing a condition, disease or disorder, said method comprising administering to a subject in need a therapeutically effective amount of the formulation as defined in any previous claim. In some embodiments, for example where the composition is a vaccine and the agent is a prophylactic, the method of preventing disease includes immunization. Usefully therefore, the invention enables a new efficient and effective means by which patient compliant vaccination can take place. The method of treatment may include vaccination for any of the diseases or against any of the viruses which are associated with said diseases as listed herein.

Further still, the invention described herein further concerns a new process for manufacturing tablets which retains the characteristic requirements needed when used for needle-free delivery. In particular, the invention concerns a method of producing a tablet comprising the solid dose formulation according to any previous claim by: combining the components of the solid dose formulation in a dry powder form; directly compressing the powder in a die; and drying the solid dose formulation at a temperature from 25° C. to 40° C., for at least 24 hours.

In embodiments, the process above is for making micro tablets, preferably elongate micro tablets. In embodiments, the die is configured to produce a tablet with a size with a diameter of 0.5 to 2 mm, preferably 0.75 mm to 2 mm and most preferably 0.85. Tablets with a wider diameter may not be desirable, as they may increase the sensation felt by the recipient; reducing patient compliance associated with this type of administration.

The die itself may be elongate and/or have diameter of 0.5 mm to 2 mm, preferably 0.75 mm to 1.2 mm. More preferably, the die is about 0.85 mm in diameter.

In some examples, the drying step comprises drying at approximately 25° C. to 40° C., for 1 to 11 days under vacuum. In some examples, the drying is at approximately 10 mbar and/or at approximately 25° C. In preferred embodiments of the inventive process, combining the components may include spray drying or freeze drying the dextran with one or more of the other components of the formulation, prior to the compressing step.

The invention further concerns a novel method of producing a tablet comprising a solid dose formulation including at least one therapeutic and/or prophylactic agent, dextran and at least one excipient, the method comprising: combining the components of the solid dose formulation into a dry powder form, wherein dextran is combined with the at least one excipient by spray drying; compressing the powder in a die; and drying the solid dose formulation at approximately 25-40° C., for at least 24 hours.

The process of the invention therefore provides a particularly useful tablet, in embodiments a microtablet, with sufficient mechanical strength for needle-free delivery. The invention further concerns a method of treating or preventing a disease or disorder, said method comprising administering to a subject in need, a therapeutically effective amount of the solid dose formulation as described or produced herein in accordance with the invention.

DESCRIPTION OF THE INVENTION

Certain aspects and embodiments of the invention will now be illustrated by way of examples and with reference to the tables/figures herein.

IMPACT OF DEXTRAN VS OTHER COMPONENTS ON TABLET STRENGTH

It is desirable to understand the impact on compressive strength of the final tablet when the dextran as a percentage of the composition is varied in accordance with different excipients.

To this end, different blends of compositions with 29.7%, 49.5% and 99% dextran were tableted with 1% of a lubricant, Sodium Stearyl Fumarate (SSF) and CMC.

Where required, mannitol was used as the excipient to make up the composition to 100% (w/w).

A comparison composition of 99% CMC and 1% lubricant was also tested. The resulting tablets were dried at 40° C. in a vacuum oven at 10 mbar for 24 hours and then tested for compression strength.

The data shows that dextran impacts desirably on the blends within the composition, consistently conferring a desirable compressive strength (at least 80 MPa) to the tablet alone and in some examples in combination with CMC and or mannitol, helping to improve or maintain that strength).

99% Dextran was shown to provide a strength well in excess of that which is needed for the present invention 148 MPa (as compared to 80 MPa) confirming that this component conveys specific strength useful in this type of needle-free solid dose formulation. In contrast, CMC or mannitol alone conferred an insufficient compressive strength to the resulting tablet, well below what is required for this application.

Furthermore, from the extrapolated curve of the graphical analysis, 66% of dextran alone appears sufficient to retain a technically acceptable compressive strength of 80 MPa.

The graphical analysis confirms that CMC (sometimes in combination with mannitol) can be combined with dextran to retain acceptable compressive strength. However, if CMC and dextran are combined alone, in specific percentages the compressive strength can be maintained or enhanced.

However, such combinations do not reach the strength post drying achieved by use of dextran in high percentage alone suggesting strongly (particularly as it relates to FIG. 2) that CMC is not the major strength giving factor in the final tested tablet composition.

Figure 1:
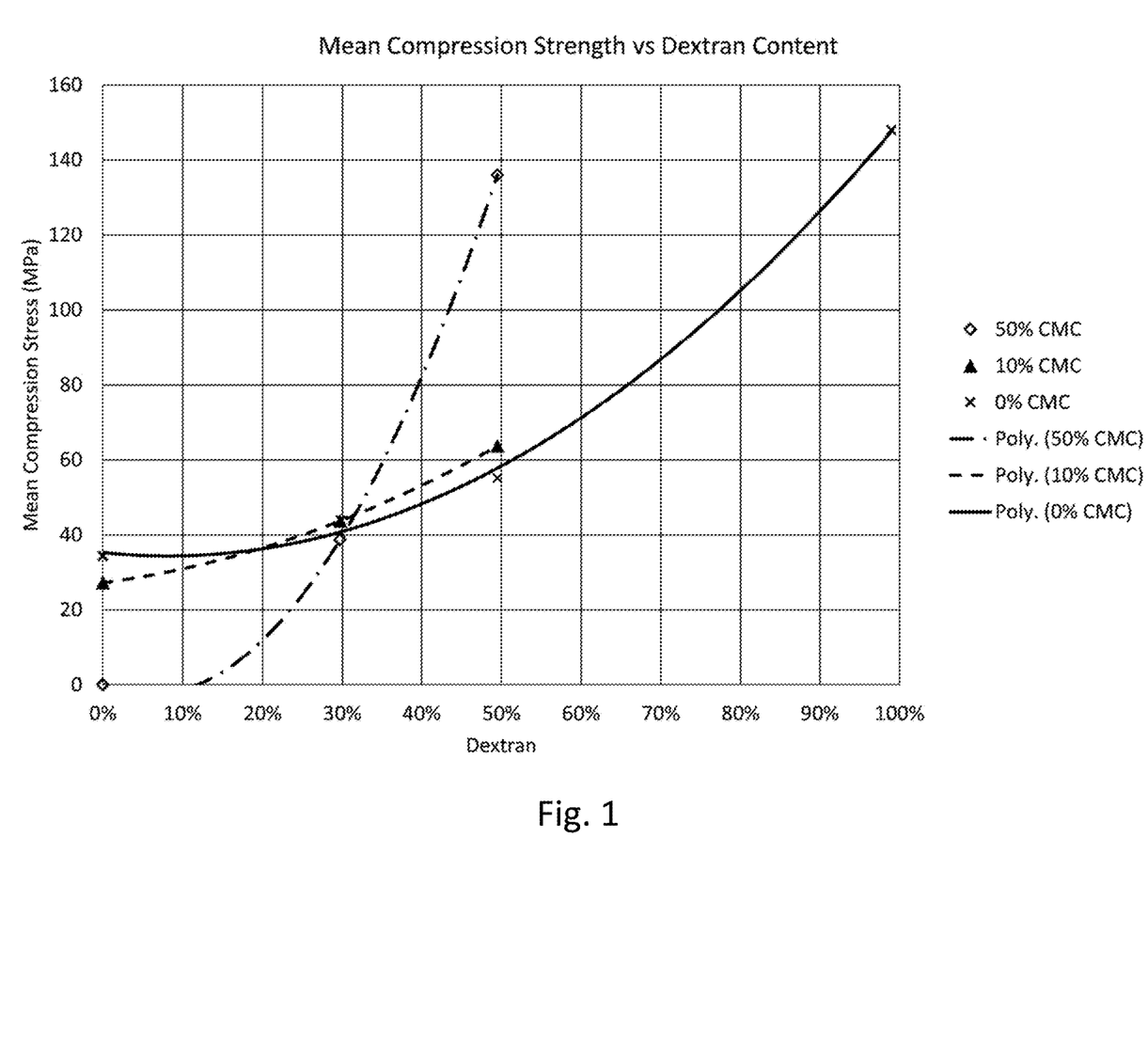
FIG. 1 shows compression stress (MPa) plotted against dextran content (%) for 2 mm diameter tablets when CMC content (%) is varied.
Figure 2:
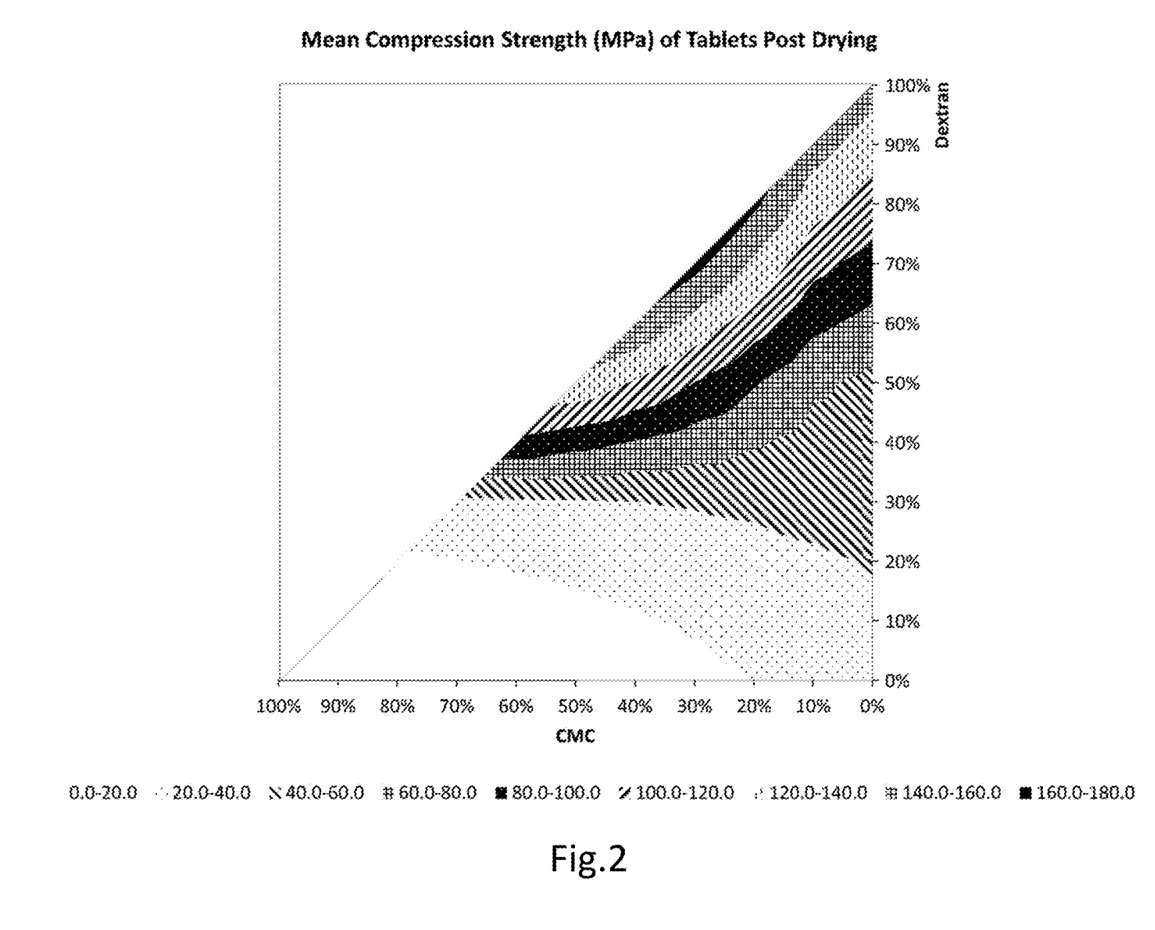
FIG. 2 shows a contour plot how varying the percentage % (w/w) of dextran and CMC impacts mean compressive strength (MPa) of the resulting 2 mm diameter tablet.

The following table lists the results and further the extrapolated percentages for a working range when the desired strength (80 MPa) is selected from the curve in the graph, provided in FIG. 1 or FIG. 2.

| Sodium carboxymethyl cellulose salt (CMC) | Mannitol | Dextran 70 | Sodium Stearyl Fumarate (SSF) | Compressive Strength after drying (MPa) |
|---|---|---|---|---|
| — | — | 99% | 1% | 148 |
| — | 33% | 66% | 1% | 80 (FIG. 1) |
| 36% | — | 63% | 1% | 80 (FIG. 2) |
| 10% | 39% | 50% | 1% | 80 (FIG. 2) |
| 49.5% | — | 49.5% | 1% | 136 |
| 50% | 9% | 40% | 1% | 80 (FIG. 1) |
| 49.5% | 19.9% | 29.7% | 1% | 40 |
| 99% | — | — | 1% | — Insufficient robustness to test |
| — | 69.2% | 29.8% | 1% | 44 |
| — | 99% | — | 1% | 34 |

Dextran Concentration on Compressive Strength

Further, the following formulations with the following compositions which were made as listed in the table below:

| Dextran 70 | Mannitol | CMC | Trehalose | Magnesium Stearate (MgS) | Mean ejection force (N) | Mean compressive strength after drying (MPa) |
|---|---|---|---|---|---|---|
| 99% | — | — | — | 1% | 0.98 | 132 |
| 98% | 1% | — | — | 1% | 1.13 | 131 |
| 95% | 4% | — | — | 1% | 1.13 | 128 |
| 90% | 9% | — | — | 1% | 1.43 | 128 |
| 74% | 25% | — | — | 1% | 2.15 | 131 |
| 49% | 50% | — | — | 1% | 3.67 | 116 |
| 25% | 74% | — | — | 1% | 7.89 | 89.2 |
| 24% | 75% | — | — | 1% | — | — |
| 98% | — | 1% | — | 1% | 0.75 | 138 |
| 95% | — | 4% | — | 1% | 0.63 | 146 |
| 90% | — | 9% | — | 1% | 0.65 | 140 |
| 74% | — | 25% | — | 1% | 0.62 | 122 |
| 49% | — | 50% | — | 1% | 0.61 | 80.7 |
| 25% | — | 74% | — | 1% | 0.76 | 29.8 |
| 24% | — | 75% | — | 1% | — | — |
| 98% | — | — | 1% | 1% | 2.25 | 132 |
| 95% | — | — | 4% | 1% | 2.79 | 134 |
| 90% | — | — | 9% | 1% | 2.46 | 136 |
| 74% | — | — | 25% | 1% | 4.17 | 128 |
| 49% | — | — | 50% | 1% | 7.56 | 108 |
| 25% | — | — | 74% | 1% | 9.71 | 77.9 |
| 24% | — | — | 75% | 1% | — | — |

It is desirable to understand the impact on compressive strength when the dextran concentration as a percentage of the composition changes in accordance with different excipients. Blends of the above compositions were tabletted in a 1 mm die.

After vacuum drying at 25° C. for 5 days, each tablet was tested for its compressive strength.

Figure 3A:
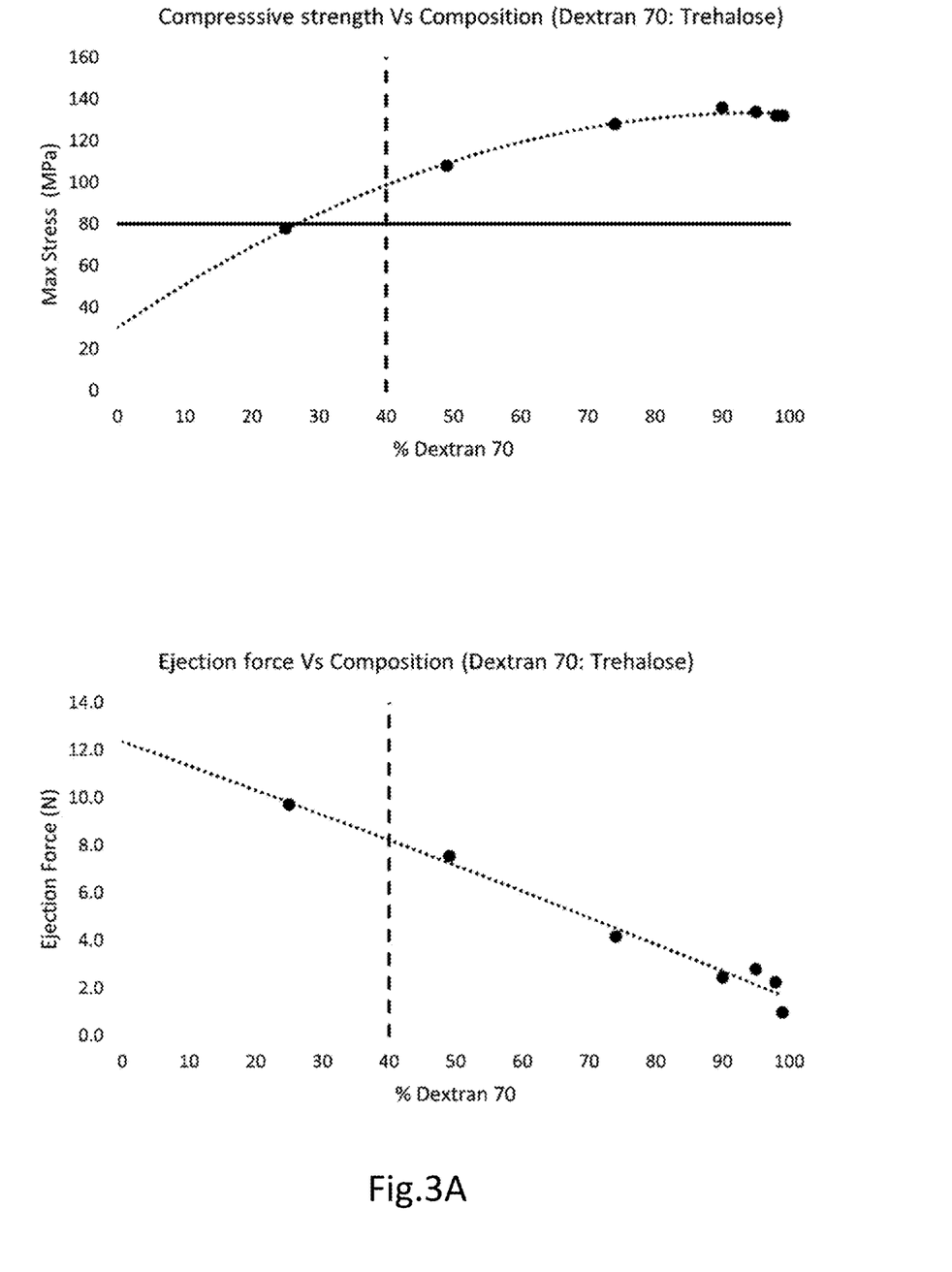
FIGS. 3A, 3B and 3C show the impact dextran concentration as a percentage (w/w) of the composition has on mean compressive strength (MPa) and ejection force (kg) of the resulting 1 mm diameter tablet in accordance with different excipient combinations.
Figure 3B:
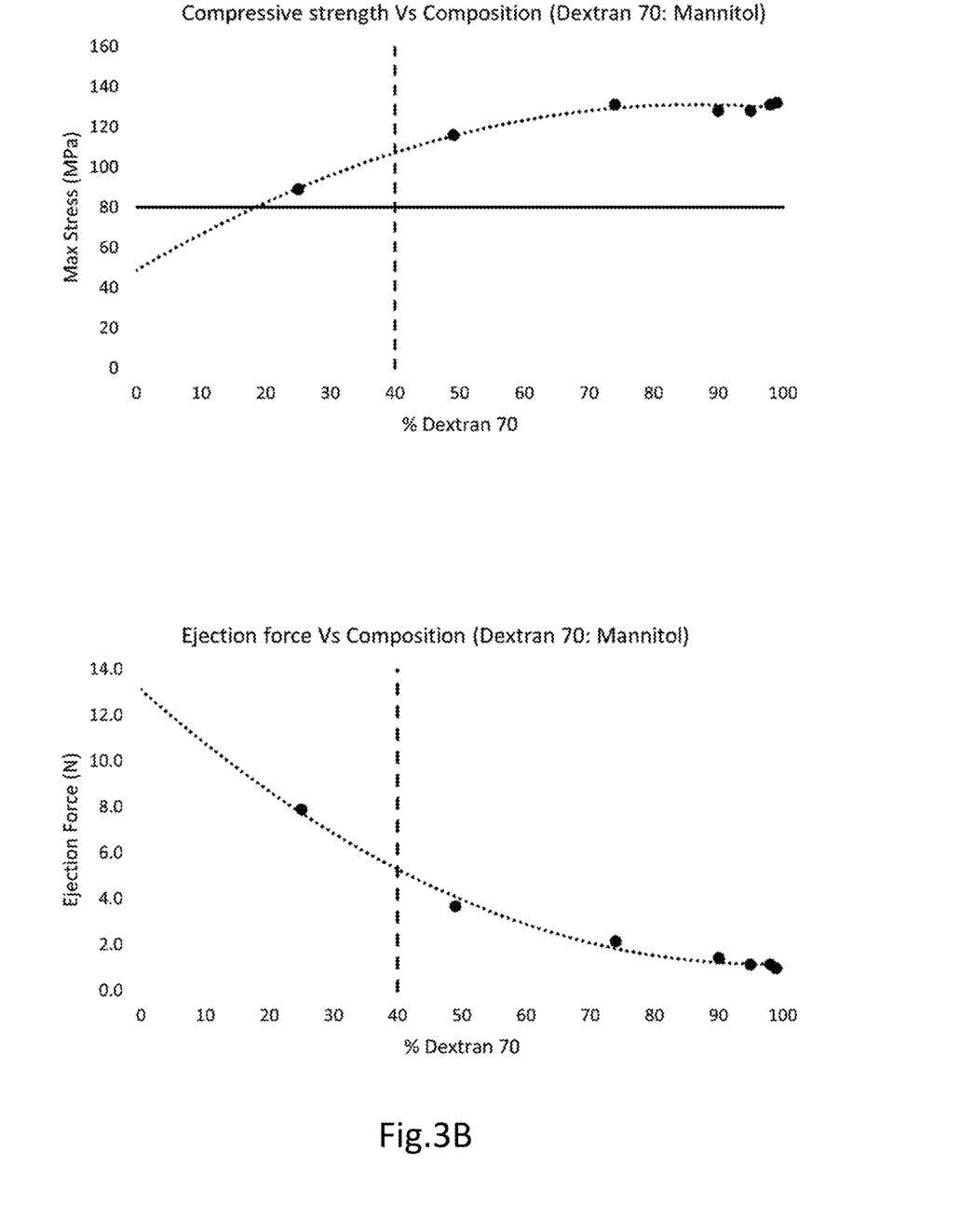
Figure 3C:
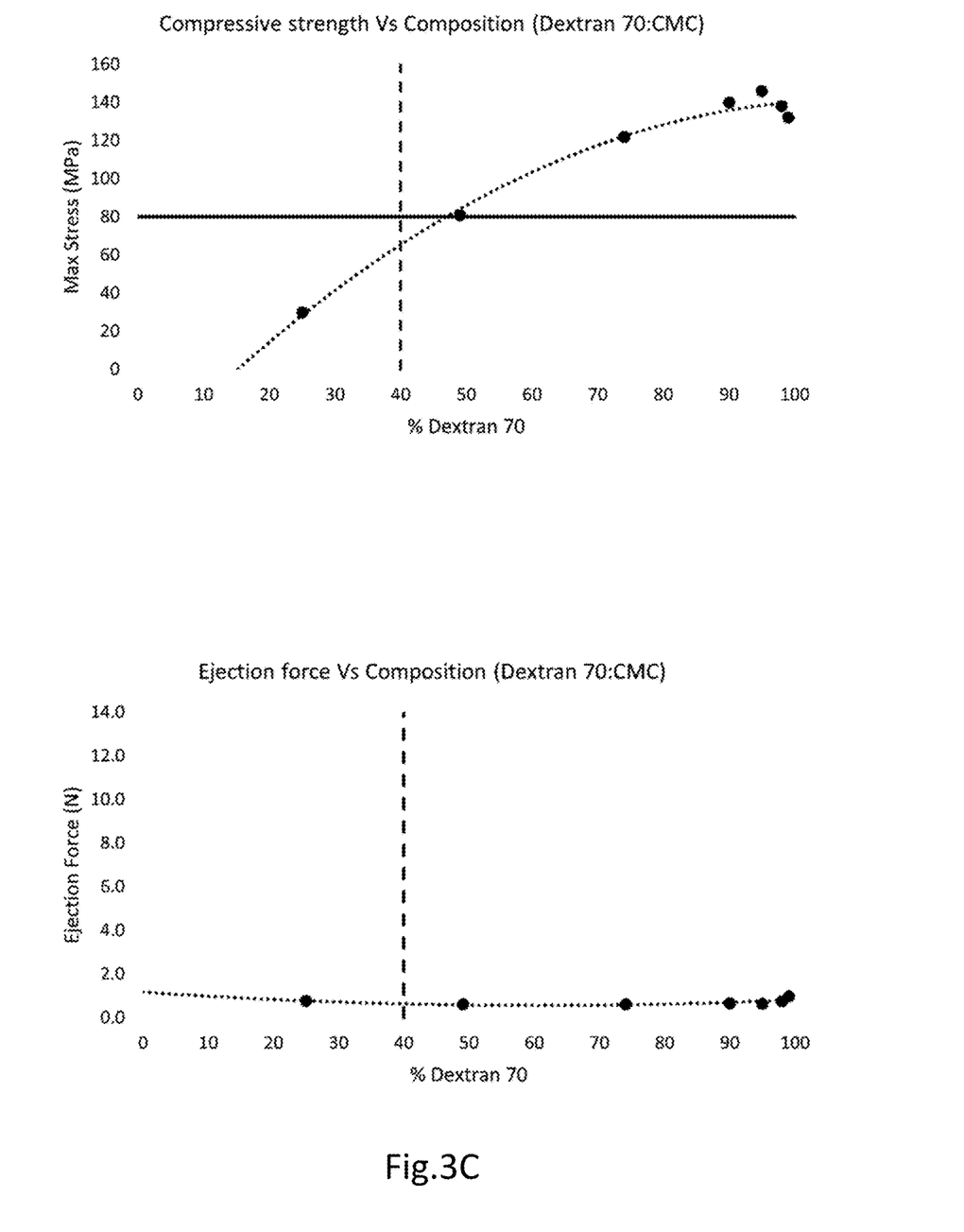

The data show that a substantial percentage of dextran within the composition consistently confers a desirable compressive strength (at least 80 MPa) to the solid dose. The data also show that in certain embodiments, Dextran 70 content can be as low as 25% (w/w) and confer sufficient mechanical strength. A clear trend can be seen in FIG. 3 showing a reduction in mean ejection force (kg) with increased dextran content irrespective of the second excipient combined with dextran.

Excipient Selection in Processing

Ejection force is the force required to eject the compressed tablet from the tableting machinery. Ejection involves breaking the adhesions between the die wall and compact surface. Heat is generated when the tablet is ejected from the tableting machinery through friction between the tablet and the die wall. Absorption of this heat leads to bond formation. Lubrication is necessary to reduce ejection forces and reduce the risk of tablet defects post-unloading. For the purpose of administering a suitable needle-free solid dose formulation parenterally in humans, it is necessary to find a parenterally acceptable tableting lubricant. A lubricant identified was magnesium stearate (MgS). It was desirable to compare the ejection force (from the die) of dextran 70 blended with MgS as compared to sodium stearyl fumarate (SSF)—one of the most commonly used lubricants in tableting processes. Lubricants were tested in quantities ranging from 0.5 to 5.0% of the total blend comprising otherwise pure dextran. Blends of the resulting formulations were tableted in a 2 mm die and ejection forces of the resulting tablets were measured.

| Lubricants | Amount added (%) | Mean ejection force (kg) |
|---|---|---|
| SSF | 0.5 | 1.39 |
|  | 1.0 | 1.52 |
|  | 2.0 | 1.33 |
| MgS | 0.5 | 1.71 |
|  | 1.0 | 1.33 |
|  | 2.0 | 1.25 |
|  | 5.0 | 1.36 |

The ejection force of tablets comprising MgS was comparable to those prepared using SSF and therefore MgS was deemed to represent a useful alternative suitable for the manufacturing type and purpose. These results suggest that MgS is a particularly suitable lubricant for tableting manufacturing across the percentage range shown.

Grade of Dextran

Dextran is a generic term for a family of glucopolysaccharides made by polymerization of the α-d-glucopyranosyl moiety of sucrose in a reaction catalysed by the enzyme dextransucrase. The common feature is a preponderance of (1→6)-linked α-d-glucopyranosyl units.

Dextran is available in a number of different grades. It has been shown above that dextran with a mean molecular weight of 70 kDa provides good compressive strength. In this example, further grades of dextran were tested.

Formulations consisting of dextran and 1% magnesium stearate were tableted at a diameter of 2 mm, and dried at 40° C. for 24 hours. Compressive strength testing was conducted after drying.

| Dextran grade Mean mw (kDa) | Mean compressive strength (MPa) |
|---|---|
| 1 | 73 |
| 10 | 117 |
| 40 | 110 |
| 110 | 104 |

The results show that all the grades tested were able to achieve the desired compressive strength of at least about 80 MPa, with the exception of dextran that had a mean molecular weight of 1 kDa.

Processing Techniques

Furthermore, to check the effect of processing steps on strength, such as the method of combining components of the formulation, two further examples were prepared as follows but the step of spray drying was used to combine them.

| Dextran 70 | Component | Lubricant (1%) | Mean compressive strength (MPa) |
|---|---|---|---|
| 79.2% | Trehalose (19.8%) | Magnesium stearate (MgS) | 137 |
| 96.5% | Lysozyme (2.5%) | Magnesium stearate (MgS) | 148 |

The base solid dose composition comprised dextran and trehalose or lysozyme with a further 1% (w/w) of lubricant. Tablets were formed with a diameter of 0.85 mm. The resulting tablets were dried at 40° C. in a vacuum oven at 10 mbar for 5 days.

The mean compressive strength was tested and considered superior in these examples, suggesting spray drying may have a very positive impact when combining excipients with dextran during the tableting process.

Compressive Strength, Drying and Moisture Content

Formulations consisting of dextran with a mean molecular weight of 70 kDa and 1% magnesium stearate were tableted at a diameter of 2 mm.

The resulting tablets were set at various drying conditions:

Room temperature

25° C. in a vacuum oven at 10 mbar

40° C. in a vacuum oven at 10 mbar

25° C. in a sealed container with desiccant

The resulting compressive strength and moisture content for each drying condition was evaluated at the following time points:

1 day 5 days 11 days

| Drying conditions | Drying time (days) | Compressive strength (MPa) | Moisture content (%) |
|---|---|---|---|
| Room temperature | 0 | 66 | 4.7 |
| Vacuum oven 25° C. | 1 | 65 | 4.5 |
|  | 5 | 84 | 3.8 |
|  | 11 | 84 | 3.0 |
| Vacuum oven 40° C. | 11 | 98 | 1.8 |
| Desiccant 25° C. | 1 | 72 | 3.8 |
|  | 5 | 86 | 3.0 |
|  | 11 | 94 | 2.3 |

The results show a clear inverse relationship between the moisture content of the tablet and its compressive strength at all conditions tested. For 2 mm tablets, 5 and 11 days drying resulted in tablets with sufficient compressive strength at all drying conditions.

In addition, a formulation consisting of dextran with a mean molecular weight of 70 kDa and 1% magnesium stearate was tableted at a diameter of 1.2 mm. The resulting tablets were dried at 40° C. in a vacuum oven at 10 mbar for 24 hours and found to have a compressive strength above 80 MPa.

| Drying conditions | Drying time (days) | Compressive strength (MPa) |
|---|---|---|
| Vacuum oven 40° C. | 1 | 91 |

The results clearly demonstrate that temperature, period of drying and mode are relevant in a given drying process during manufacture of this type of solid dose tablets; the resulting compressive strength may be adversely affected, if suitable conditions are not selected.

Tablet Size

Tablets have also been manufactured by the applicants using different diameter dies.

Tablets were compressed in either a 2 mm (control), 1.2 mm (see above example) or 0.85 mm die. Tablets were then dried for 24 hrs at 10 mbar with the temperatures specified. Compressive strength of the tablets was conducted before and after drying.

| Die size (mm) | Powder mass | Drying temperature (° C.) | Drying time (days) | Compressive strength (MPa) |
|---|---|---|---|---|
| 2.0 (Control) | 20 mg | 25° C. | 5 | 84 |
| 1.2 | 7 mg | 40° C. | 5 | 91 |
| 0.85 | 4 mg | 25° C. | 5 | 95 |

The compressive strength at both diameters tested was still above 80 MPa. It is therefore observed that tablets of sufficient compressive strength can be obtained at a range of diameters below 2.0 mm, and particularly in the range 0.85 to 2.0 mm, demonstrating the composition may be used to produce a microtablet which retains suitability for needle-free delivery injection.

In embodiments, compositions with increased dextran content confer reduced ejection force which is advantageous in the tablet manufacturing process. High ejection force is associated with a higher risk of tablet defects post-unloading and can be used as a metric to identify and mitigate these risks. Moreover, high ejection force indicates that the formulation is at risk of sticking and/or picking. It is a measure of how well lubricated the formulation is; poor lubrication results in tablet defects such as picking, sticking and capping whereas over lubrication reduces tablet hardness. Lastly, high ejection force can lead to increased mechanical wear.

In examples, dextran may be provided at the lower end of the range, such as 25-49% (w/w) dextran, the bulk of the tablet may be made up with a different excipient, for example, an excipient selected from the group of trehalose, mannitol, or CMC and/or in a range of at least 50-74% (w/w)

In examples wherein the formulation comprises dextran, at less than 40% or less than 30%, and an excipient is combined with dextran, the ratio is thought to maintain or consolidate mechanical strength to achieve the minimum compressive strength required for needle-free delivery of a solid composition.

In some cases, as demonstrated in FIGS. 3A and 3B, for example formulations that comprise dextran below 40% (w/w) may still exhibit sufficient mechanical strength when present at least 25% (w/w) with a different excipient in an appropriate ratio. This has been shown particularly when the different excipient is selected from the group of trehalose and mannitol. In such examples, the second excipient makes up the majority of the bulk composition with dextran.

In examples, the formulation comprises at least 27% dextran, more particularly, at least 28% (w/w) dextran and at least 70% (w/w) of said second excipient. The excipient selected may be trehalose as shown in FIG. 3A to achieve an compressive strength of at least 80 MPa.

In examples, the formulation comprises at least 25% dextran (w/w) and at least 73% (w/w) of a further excipient. For example, when the excipient selected is mannitol it is possible to achieve a compressive strength of at least 80 MPa, as shown in FIG. 3B, In examples, the excipient may additionally or alternatively be a stabiliser such as $MgCl_2$, $MgSO_4$, lactose-sorbitol, sorbitol-gelatine or tris-EDTA, a binding agent such as povidone, starch, gelatin or alginate, or a bulking agent such as mannitol, sucrose, CMC, trehalose, PLGA, PVP, PVA or PLA.

In some cases, as demonstrated in FIG. 3C, example formulations that comprise dextran as low as 49% and still exhibit sufficient mechanical strength when combined with a further excipients in an appropriate ratio, this has been shown particularly wherein the second excipient (additional to the dextran) is CMC.

Compressive Strength Testing with Formulated API Compositions

It is imperative to understand what impact, if any, the at least one therapeutic and/or prophylactic agent has on compressive strength.

To evaluate whether this property is altered by the inclusion of API different blends of compositions formulated with 0.125%, 0.250% and 0.625% API (w/w) (vaccine) were tableted with 89% dextran (w/w) and 1% lubricant (w/w). Producing these formulations involved freeze drying 10% of the total powders including the vaccine before the tableting process.

The following formulations with the following compositions were made as listed in the table below.

| Formulation details | | | | | | | | |
|---|---|---|---|---|---|---|---|---|
| Included in freeze dried matrix (10% of total powders) | | | | | | Bulk powders | | Max |
| Mannitol | PVP | Dextran 70 | Sucrose | Tris-EDTA | Vaccine | Dextran 70 | Magnesium stearate | stress (MPa) |
| 2.00% | 0.20% | 6.644% | 1.00% | 0.031% | 0.125% | 89% | 1% | 137 |
| 2.00% | 0.20% | 6.489% | 1.00% | 0.061% | 0.250% | 89% | 1% | 138 |
| 2.00% | 0.20% | 6.032% | 1.00% | 0.152% | 0.625% | 89% | 1% | 134 |

The resulting tablets were 1 mm in diameter and manufactured using 100 kg compaction force. All tablets were dried at 25° C. at 10 mbar for 5 days and found to have a compressive strength above 80 MPa.

The data show that vaccine within the range of 0.125%-0.625% (w/w) has no discernible impact on compressive strength where bulk dextran content is 89% (w/w), mannitol content is 2.0% (w/w), PVP content is 0.20% (w/w), sucrose content is 1% (w/w) and MgS content is 1% (w/w).

The applicants therefore conclude that any of the compositions of the invention maybe successfully formulated with API, for example vaccine-based API, to yield a solid dose suitable for needle-free delivery, as the compressive strength is able to be maintained.

The invention claimed is:

1. A solid dose formulation having a compressive strength of at least about 80 MPa for needle-free delivery comprising:
   0.01%-25.0% (w/w) of at least one therapeutic and/or prophylactic agent;
   at least 25.0% (w/w) of dextran; and
   at least 50% (w/w) of at least one, or combination of two or more, different excipients, excluding dextran.

2. The solid dose formulation according to claim 1, wherein the excipient or excipients are selected from the group consisting of trehalose, mannitol and CMC.

3. The solid dose formulation according to claim 1, further comprising at least 0.5% (w/w) of a lubricant.

4. The solid dose formulation according to claim 1, wherein the at least one therapeutic and/or prophylactic agent is an immunogen.

5. The solid dose formulation according to claim 1, wherein the at least one therapeutic and/or prophylactic agent is a biological or chemical preparation selected from the group consisting of a vector, a protein, a protein subunit, DNA, RNA, a toxoid or a polysaccharide-antigen conjugate, and a checkpoint inhibitor.

6. The solid dose formulation according to claim 1, wherein the solid dose formulation comprises dextran in the range of 40-99%.

7. The solid dose formulation according to claim 1, wherein the dextran is selected from a grade with a mean molecular weight between 10 kDa and 110 kDa.

8. The solid dose formulation according to claim 1, wherein the dextran selected includes 0.5% to 6% (w/w) water.

9. The solid dose formulation according to claim 1, wherein the solid dose formulation is a tablet or micro tablet, and/or is elongated.

10. The solid dose formulation according to claim 1, wherein the solid dose formulation has a length to width ratio from 2:1 to 6:1.

11. The solid dose formulation according to claim 1, wherein the solid dose formulation has a width from 0.5 mm to 2 mm and a length from 1.7 to 12 mm.

12. The solid dose formulation according to claim 9, wherein the tablet or micro tablet has a pointed tip with an internal angle of between 22.5° and 90°.

13. The solid dose formulation according to claim 1, further comprising one or more of methionine, cysteine, histidine, citric acid, sodium chloride, sodium hydroxide, hydrochloric acid, potassium chloride, tween-20, tween-40, tween-60, tween-80, albumin, mannitol, trehalose, sucrose, sodium carboxymethylcellulose salt, or a combination thereof.

14. The solid dose formulation according to claim 3, wherein the lubricant is magnesium stearate.

15. The solid dose formulation according to claim 1, wherein the formulation further comprises CMC, in the range of 10-50% (w/w) and 9-39% (w/w) mannitol.

16. A method of treatment or prevention of one or more diseases or disorders, the method comprising:
   providing a solid dose formulation having a compressive strength of at least about 80 MPa for needle-free delivery comprising:
   0.01%-25.0% (w/w) of at least one therapeutic and/or prophylactic agent;
   at least 25.0% (w/w) of dextran; and
   at least 50% (w/w) of at least one, or combination of two or more, different excipients, excluding dextran; and
   using a needle-free delivery device, administering a therapeutically-effective amount of said solid dose formulation to a patient.

17. The method of treatment or prevention of one or more diseases or disorders of claim 16 wherein the disease or disorder is selected from the group consisting of: cancer, yellow fever, rabies, diphtheria, tetanus, haemophilus influenza type B (Hib), pertussis, pneumococcal diseases, meningococcal diseases, human papilloma viruses (HPV), HTV, HSV2/HSV1, influenza types A, B and C, para influenza, polio, RSV, rhinoviruses, rotaviruses, hepatitis A, acquired immunodeficiency syndrome (AIDS), anthrax, gastroenteritis, enterovirus diseases, measles, mumps, varicella zoster, glandular fever, respiratory diseases, rubella, human T-cell lymphoma type I (HTLV-I), hepatitis B, hepatitis C, hepatitis D, poxvirus diseases, cholera, Japanese encephalitis, zika, chikungunya, bat lyssavirus, Q fever, rift valley fever, hendra virus, tularaemia, nipah virus, lassa fever, typhoid fever, Crimean-Congo hemorrhagic fever, ebola, plague and shigella, or against veterinary diseases, comprising foot and mouth disease serotypes O, A, C, SAT-1, SAT-2, SAT-3 and Asia-1, coronavirus, bluetongue, feline leukaemia, avian influenza, hendra and nipah virus, pestivirus, canine parvovirus, and bovine viral diarrhoea virus.

18. The method of treatment or prevention of one or more diseases or disorders of claim 16 wherein the solid dose formulation further comprises:
   at least 0.5% (w/w) of a lubricant;
   one or more of methionine, cysteine, histidine, citric acid, sodium chloride, sodium hydroxide, hydrochloric acid, potassium chloride, tween-20, tween-40, tween 60, tween-80, albumin, mannitol, trehalose, sucrose, sodium carboxymethylcellulose salt, or a combination thereof;
   wherein the at least one therapeutic and/or prophylactic agent is a biological or chemical preparation selected from the group consisting of a vector, a protein, a protein subunit, DNA, RNA, a toxoid or a polysaccharide-antigen conjugate, and a checkpoint inhibitor, and wherein the excipient or excipients are selected from the group consisting of trehalose, mannitol and CMC.

19. The method of treatment or prevention of one or more diseases or disorders of claim 16 wherein the solid dose formulation is a tablet or micro tablet having a pointed tip with an internal angle of between 22.5° and 90°.

20. A method of vaccinating a patient against one or more diseases or disorders, the method comprising:

providing a solid dose formulation having a compressive strength of at least about 80 MPa for needle-free delivery comprising:

0.01%-25.0% (w/w) of at least one therapeutic and/or prophylactic agent;

at least 25.0% (w/w) of dextran; and at least 50% (w/w) of at least one, or combination of two or more, different excipients, excluding dextran; and using a needle-free delivery device, administering a therapeutically-effective amount of said solid dose formulation to a patient.

* * * * *